(12) United States Patent
Bain et al.

(10) Patent No.: US 9,304,103 B2
(45) Date of Patent: Apr. 5, 2016

(54) SELF-CALIBRATING ION METER

(71) Applicant: SENTIENT TECHNOLOGIES, INC., Los Gatos, CA (US)

(72) Inventors: Mark Bain, Mountain View, CA (US); Frederick Quincy Johnson, Pleasanton, CA (US)

(73) Assignee: Sentient Technologies, Inc., Los Gatos, CA (US)

( * ) Notice: Subject to any disclaimer, the term of this patent is extended or adjusted under 35 U.S.C. 154(b) by 496 days.

(21) Appl. No.: 13/629,056

(22) Filed: Sep. 27, 2012

(65) Prior Publication Data

US 2013/0085701 A1     Apr. 4, 2013

Related U.S. Application Data

(60) Provisional application No. 61/541,900, filed on Sep. 30, 2011.

(51) Int. Cl.
*G01F 19/00*     (2006.01)
*G01N 27/414*    (2006.01)

(52) U.S. Cl.
CPC .................. *G01N 27/4148* (2013.01)

(58) Field of Classification Search
CPC ..... B82Y 15/00; B82Y 30/00; G01N 27/3277
USPC ......................... 702/104, 182–185
See application file for complete search history.

(56) References Cited

U.S. PATENT DOCUMENTS

| | | | |
|---|---|---|---|
| 5,223,117 A * | 6/1993 | Wrighton et al. | 204/415 |
| 2012/0171715 A1* | 7/2012 | Thalhammer et al. | 435/29 |
| 2013/0084214 A1* | 4/2013 | Johnson et al. | 422/82.03 |

FOREIGN PATENT DOCUMENTS

| | | |
|---|---|---|
| GB | 2451596 | 2/2009 |
| WO | 2010/142773 | 12/2010 |

* cited by examiner

*Primary Examiner* — Edward Raymond
(74) *Attorney, Agent, or Firm* — Fish & Tsang, LLP

(57) ABSTRACT

An ion meter is calibrated by providing two ISFETS with different areas, where the two gate areas are used to calibrate the two ISFETS with respect to one another. The use of two ISFET gates that can be calibrated with respect to one another eliminates the need for an ion meter to be recalibrated before every use, and allows the ion meter to measure the concentration in the solution over an extended period of time.

12 Claims, 3 Drawing Sheets

SELF-CALIBRATING ION METER

This application claims priority to U.S. provisional application Ser. No. 61/541,900 filed Sep. 30, 2011.

FIELD OF THE INVENTION

The field of the invention is ion meter systems and methods.

BACKGROUND

It is known to use ion-sensitive field effect transistor (ISFET) devices to measure the concentration of ions in a solution. However, ISFET devices frequently need to be recalibrated since pH electrodes tend to change in resistive properties over time. GB2451596 to Kahn teaches an ISFET device whose surface is modified with semiconductor sensors and do not require calibration for a few days after a first use. However, Kahn's ISFET device still requires recalibration after a week's time.

WO2010142773 to Thalhammer teaches an ISFET device that calibrates itself by providing multiple identical ISFET transistors, where one or two of the ISFET transistors might be constantly exposed to a calibration substance which would allow the system to estimate how other pH electrodes might change in resistive properties over time. Thalhammer's system is still imperfect, since not all ISFET transistor electrodes are completely identical, and they cannot all change in resistive properties in the same manner over time.

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

Thus, there is still a need for improved systems and methods for calibrating an ion meter.

SUMMARY OF THE INVENTION

The inventive subject matter provides apparatus, systems and methods in which an ion meter is calibrated by providing two ISFETS with different areas, where the two gate areas are used to calibrate the two ISFETS with respect to one another. The use of two ISFET gates that can be calibrated with respect to one another eliminates the need for an ion meter to be recalibrated before every use, and allows the ion meter to measure the concentration in the solution over an extended period of time.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Figure 1:
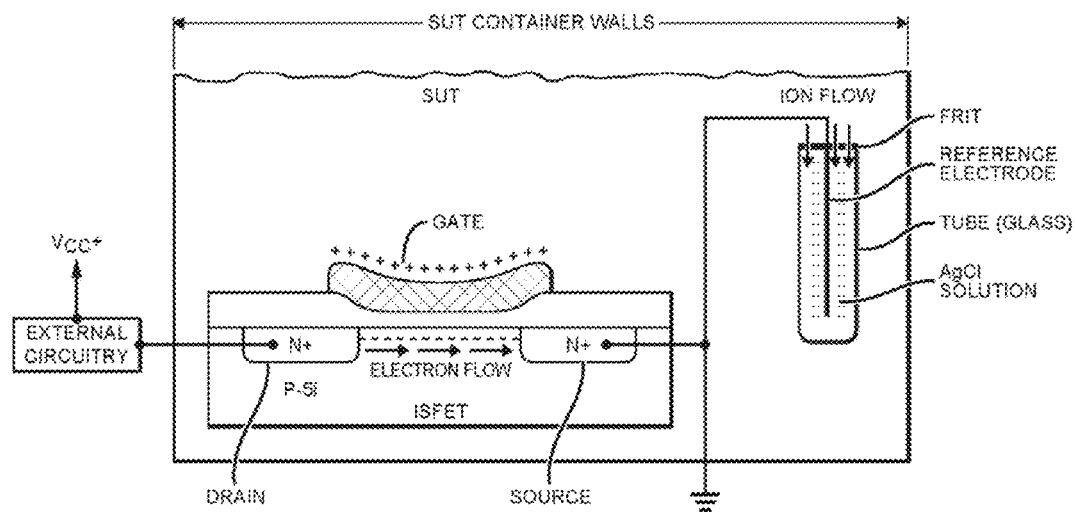
FIG. 1 is a schematic of a prior art ISFET device submerged within a solution under test.

In FIG. 1, a prior art ISFET device is shown submerged within a solution under test (SUT) having an battery external to the SUT coupled to a drain of the ISFET, and having a reference electrode and a ground coupled to a source of the ISFET to allow current to flow across the gate. This allows the SUT to act as a conductor for the ions which charge the gate area of the ISFET.

The voltage difference between the source and the drain of the ISFET, and the amount of current that flows across the ISFET, is directly proportional to the concentration of ions in the SUT. If the reference electrode is ion-selective, the ISFET could be configured to be sensitive to only a certain type of electrode, thereby detecting the concentration of a given ion within the solution. Here, the reference electrode is a silver material with an AgCl coating, which interfaces with the ionizing solution, which can vary, but is preferably a supersaturated KCl and/or AgCl solution In FIG. 2 an ion meter of the present invention generally has at least two ISFET devices, each with a gate that is effectively exposed to a solution. As used herein a gate that is "effectively" exposed to a solution is one whose surface area is exposed to the solution to such an extent that an electric current can flow from a drain to a source across the gate surface. Preferably, the entire surface area of the gate is exposed to the solution. As used herein, an ion "meter" is a measuring instrument that collects data on the concentration of ions in a solution and expresses a value as a function of the data. Preferably, the ion meter is a meter that expresses the concentration of ions in a solution as a function of the molar concentration of dissolved ions within the solution. In an exemplary embodiment, the ion meter is a hydrogen ion meter that expresses the concentration of hydrogen ions in the solution in terms of pH.

Each of the two ISFET devices has a different surface area, but preferably has at least one dimension that is identical to the other. For example, is preferred that both ISFET gates have the same length but different widths, or that both ISFET gates have the same width but different lengths. As used herein, a gate "length" is a distance between two n doped channels, and can be referred to conventionally as n-channel spacing, and a gate "width" is a length of the n-channels available to provide conduction. As a gate becomes wider, fewer free electron states per unit "width" are required to carry current.

As current flows from the drain to the source of each of the ISFET devices, a circuit will measure electric activity across the two ISFET devices, such as the amount of current that flows from the source to the drain or the amount of voltage that flows from the source to the drain. That electric activity could then be translated into an ion concentration by calibrating the ISFET device using the delta between the surface areas of the two ISFET gates. Thus, for example, for the two ISFET gates shown below, the concentration of ions within the solution could be calculated as a function of the current across gate #1, the current across gate #2, and the ratio of the surface area of gate #1 to the surface area of gate #2, which is 1:2 (the length is spacing, and the width is the dimension normal to the spacing). Since the current flow at a fixed gate charge is a function of both the length and the aspect ratio of the gate, the current ratio will likely be a complex function.

Figure 3:
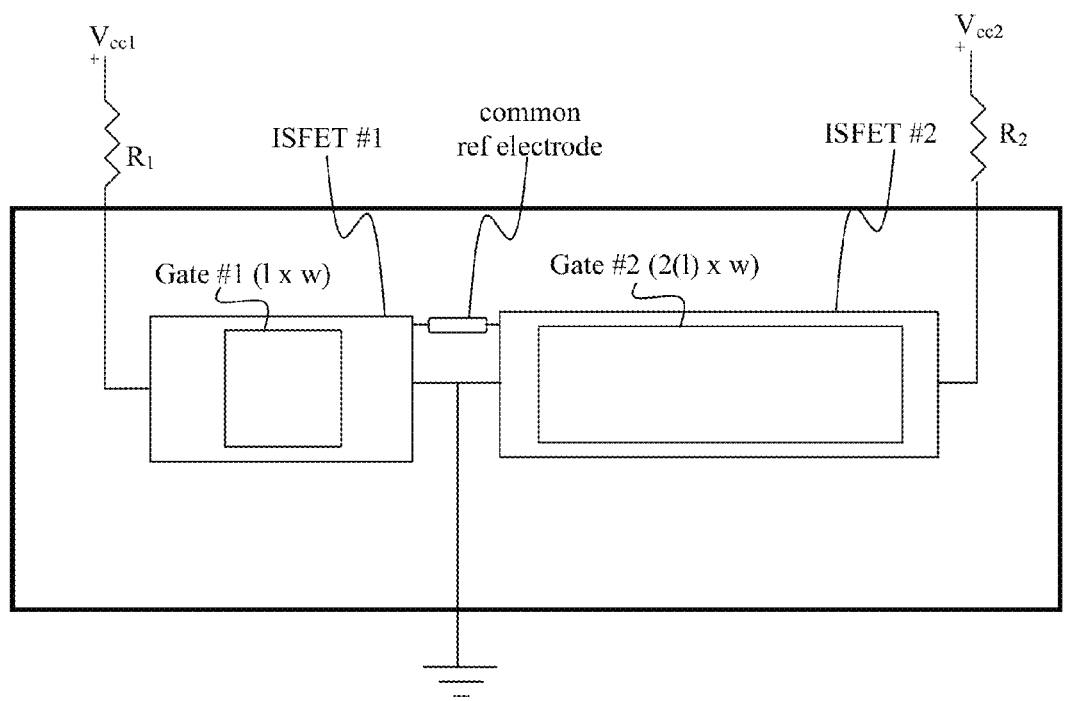
FIG. 3 is a schematic of an alternative embodiment of the present invention.

FIG. 3 depicts an embodiment in which a single reference electrode ("common ref electrode") is used for both ISFET devices. That reference electrode is preferably placed quite close in proximity to both of the ISFET gates to ensure that the gate to drain voltage gradient in the SUT is the same for both ISFET gates. In FIG. 3 the drains of both ISFET devices are coupled to a common voltage potential, and the sources of both ISFET devices are varied to ensure that the field across each gate is nearly identical. This increases the speed at which a user could gain stable readings, and reduces both temperature and light variances, as they could be nulled out.

Figure 4:
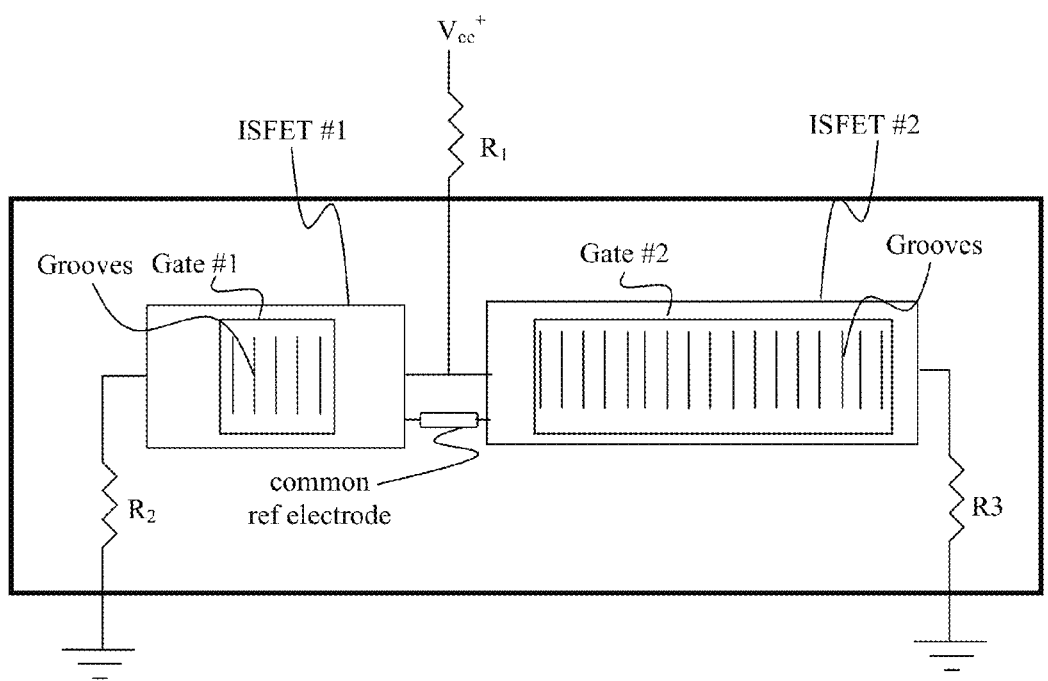
FIG. 4 is a schematic of another embodiment of the present invention.

FIG. 4 is similar to FIG. 3, except that there are two separate grounds and the surface areas of each gate is further increased by carving a series of notches or grooves into the gate surface. Preferably, the height, width, and regularity of the grooves for both ISFET gates are identical to one another to allow for easy calculation of each of the ISFET gates' surface areas relative to one another.

Figure 5:
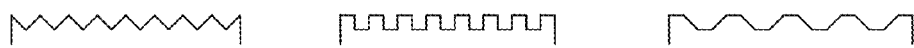
FIG. 5 is a schematic of grooves that could be formed in gates of ISFETS.

FIG. 5 shows exemplary grooves, which could be 1, 2, or 3 microns in depth and/or width, which could double or triple the surface area of each ISFET gate depending upon how wide and how tall the grooves are. While the grooves are preferably v-shaped, the grooves could be rectangular in shape or could be trapezoidal without departing from the scope of the invention. Adding such grooves modifies the way the field and electron free states interact by changing the crystallographic orientation of the silicon-silicon dioxide interface.

Figure 2:
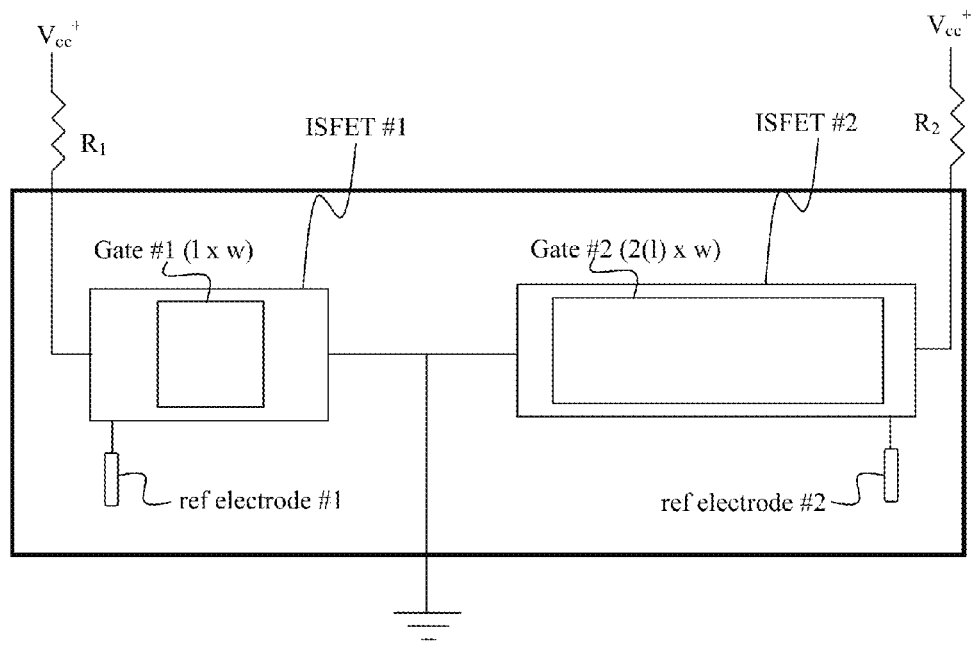
FIG. 2 is a schematic of an embodiment of the present invention.

The ISFET gates of FIGS. 2-4 should be interpreted as being formed on separate substrates, or on the same substrate. In the latter case, the gates can be isolated from one another using any number of suitable means, for example epitaxial isolation, silicon on insulators, dielectric isolation, or silicon on sapphire. More than two ISFET gates can be provided with a variety of different sizes, and each pair of ISFET gates can be isolated from one another within different testing areas so that one pair of ISFET gates are exposed to one SUT while a second pair of ISFET gates are exposed to another SUT. The doping material amounts of each of the ISFET gates are also preferably identical to one another to allow for easy calculation of the concentration of ions within the solution.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps can be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A self-calibrating ion meter that measures a concentration of an ion in a solution, comprising:
a first ISFET having a first gate with a first gate area effectively exposed to the solution;
a second ISFET having a second gate with the second gate area effectively exposed to the solution; wherein the first area effectively exposed is different from the second area effectively exposed;
a circuit that measures a first electric activity across the first ISFET and a second electric activity across the second ISFET; and
a processor that calculates the concentration when the solution is simultaneously exposed to the first gate and the second gate, wherein the concentration is calculated as a first function of the first and second electric activities, and a delta between the first and second effective areas exposed.

2. The ion meter of claim 1, wherein the first gate and the second gate are isolated from one another via epitaxial isolation.

3. The ion meter of claim 1, wherein the first width is the same as the second width.

4. The ion meter of claim 1, wherein the first gate and the second gate are both islands that are isolated from one another.

5. The ion meter of claim 1, further comprising a chip, wherein the first gate and the second gate are each mounted on the chip.

6. The ion meter of claim 1, wherein each of the first and second gates have equal concentration of a doping material.

7. The ion meter of claim 1, further comprising a first resistive drain coupled to the first gate, and a second resistive drain coupled to the second gate, wherein each of the first and second resistive drains are variable.

8. The ion meter of claim 1, wherein the ion is a hydrogen ion, and wherein the processor reports the concentration as a pH measurement.

9. The ion meter of claim 1, wherein the first gate is notched to increase a surface area of the gate.

10. The ion meter of claim 1, wherein the first gate has a notch at least 2 microns deep.

11. The ion meter of claim 1, wherein the first electric activity comprises a first drain/source voltage needed to generate a specified current across the first ISFET, and the second electric activity comprises a second drain/source voltage needed to generate the specified current across the second ISFET.

12. The ion meter of claim 1, wherein the first electric activity comprises a first current generated across the first ISFET when a specified drain/source voltage is applied to the first ISFET and the second electric activity comprises a second current generated across the second ISFET when the specified drain/source voltage is applied to the second ISFET.

* * * * *